(12) United States Patent
Adi et al.

(10) Patent No.: US 10,531,802 B2
(45) Date of Patent: Jan. 14, 2020

(54) VITAL SIGN MONITORING APPARATUSES AND METHODS OF USING SAME

(71) Applicant: MOR RESEARCH APPLICATIONS LTD., Tel Aviv (IL)

(72) Inventors: Nimrod Adi, Mazkeret Batya (IL); Gil Zoizner, Tel-Aviv (IL); Jonathan Rubin, Tel-Aviv (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 177 days.

(21) Appl. No.: 15/552,469

(22) PCT Filed: Feb. 25, 2016

(86) PCT No.: PCT/IL2016/050218
§ 371 (c)(1),
(2) Date: Aug. 21, 2017

(87) PCT Pub. No.: WO2016/135731
PCT Pub. Date: Sep. 1, 2016

(65) Prior Publication Data
US 2018/0042501 A1 Feb. 15, 2018

Related U.S. Application Data

(60) Provisional application No. 62/136,741, filed on Mar. 23, 2015, provisional application No. 62/120,545, filed on Feb. 25, 2015.

(51) Int. Cl.
*A61B 5/00* (2006.01)
*A61B 5/024* (2006.01)
(Continued)

(52) U.S. Cl.
CPC ........ *A61B 5/02416* (2013.01); *A61B 5/0004* (2013.01); *A61B 5/02055* (2013.01); *A61B 5/0295* (2013.01); *A61B 5/6806* (2013.01)

(58) Field of Classification Search
CPC .............. A61B 5/02416; A61B 5/0004; A61B 5/02055; A61B 5/0295; A61B 5/6806
(Continued)

(56) References Cited

U.S. PATENT DOCUMENTS 4,437,470 A   3/1984 Prost
5,860,932 A * 1/1999 Goto ................. A61B 5/02116
                                                    600/485
(Continued)

FOREIGN PATENT DOCUMENTS

EP          0721764 A2    7/1996

OTHER PUBLICATIONS

International Search Report of PCT/IL2016/050218 completed Jun. 14, 2016; dated Jun. 23, 2016 4 pages.
(Continued)

*Primary Examiner* — Carl H Layno
*Assistant Examiner* — Michael J Lau
(74) *Attorney, Agent, or Firm* — The Roy Gross Law Firm, LLC; Roy Gross

(57) ABSTRACT

A system for vital sign measuring of a patient, comprising: a first sensor removably attachable with a first body portion of the patient and configured to measure, when in operable position, a vital sign of the patient; at least one additional sensor removably attachable with a second body portion of the patient and configured to measure, when in operable position, a vital sign of the patient; and a processor configured to provide data descriptive of a level of correspondence between measurements of the vital signs provided by the first sensor and the at least one additional sensor.

14 Claims, 5 Drawing Sheets

(51) Int. Cl.
*A61B 5/0205* (2006.01)
*A61B 5/0295* (2006.01)

(58) Field of Classification Search
USPC .......................................................... 600/301
See application file for complete search history.

(56) References Cited

U.S. PATENT DOCUMENTS

| | | | | |
|---|---|---|---|---|
| 6,050,951 | A * | 4/2000 | Friedman | A61B 5/022 |
| | | | | 128/900 |
| 6,120,459 | A * | 9/2000 | Nitzan | A61B 5/02125 |
| | | | | 600/485 |
| 6,331,162 | B1 * | 12/2001 | Mitchell | A61B 5/02125 |
| | | | | 600/485 |
| 7,413,545 | B2 * | 8/2008 | Muramatsu | A61B 5/02241 |
| | | | | 600/301 |
| 2005/0148885 | A1 | 7/2005 | Tweed et al. | |
| 2006/0058690 | A1 * | 3/2006 | Bartnik | A61B 5/0048 |
| | | | | 600/504 |
| 2006/0253150 | A1 * | 11/2006 | McEwen | A61B 5/02233 |
| | | | | 606/202 |
| 2007/0129636 | A1 * | 6/2007 | Friedman | A61B 5/0205 |
| | | | | 600/481 |
| 2007/0225614 | A1 * | 9/2007 | Naghavi | A61B 5/01 |
| | | | | 600/549 |
| 2008/0081963 | A1 * | 4/2008 | Naghavi | A61B 5/01 |
| | | | | 600/301 |
| 2009/0287243 | A1 * | 11/2009 | Greennberg | A61H 9/0078 |
| | | | | 606/202 |
| 2011/0009754 | A1 * | 1/2011 | Wenzel | A61B 5/0215 |
| | | | | 600/485 |
| 2011/0066009 | A1 * | 3/2011 | Moon | A61B 5/0002 |
| | | | | 600/301 |
| 2011/0066041 | A1 * | 3/2011 | Pandia | A61B 5/029 |
| | | | | 600/484 |
| 2011/0137138 | A1 * | 6/2011 | Johansson | G16H 10/20 |
| | | | | 600/301 |
| 2011/0201962 | A1 * | 8/2011 | Grudic | A61B 5/021 |
| | | | | 600/561 |
| 2012/0046561 | A1 | 2/2012 | Usuda et al. | |
| 2012/0179011 | A1 * | 7/2012 | Moon | A61B 5/7207 |
| | | | | 600/324 |
| 2013/0226012 | A1 * | 8/2013 | Kinoshita | A61B 5/02108 |
| | | | | 600/490 |
| 2014/0114152 | A1 * | 4/2014 | Fournier | A61B 5/02116 |
| | | | | 600/324 |
| 2014/0135634 | A1 | 5/2014 | Pranevicius | |
| 2015/0051500 | A1 * | 2/2015 | Elliott | A61B 5/6898 |
| | | | | 600/480 |

OTHER PUBLICATIONS

Written Opinion of PCT/IL2016/050218 completed Jun. 14, 2016; dated Jun. 23, 2016 4 pages.

* cited by examiner

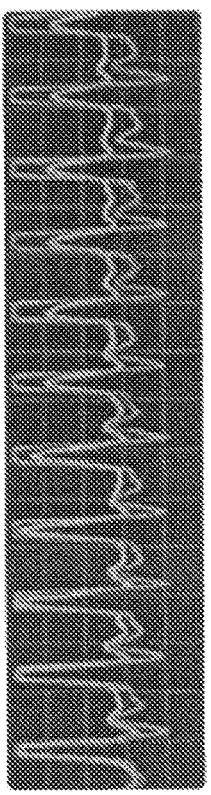
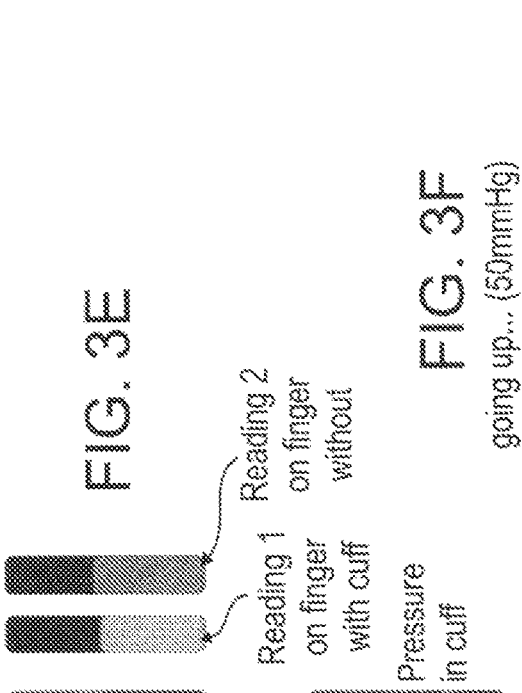
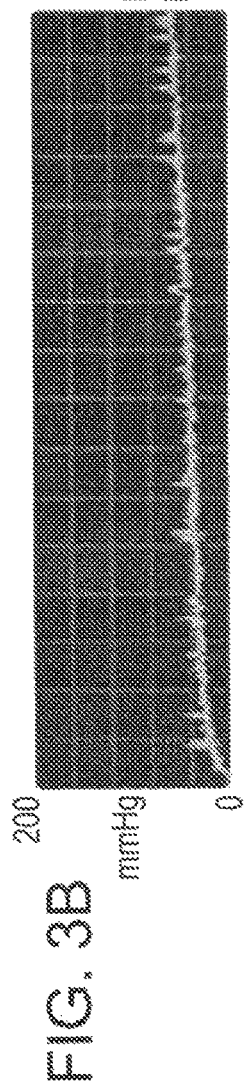
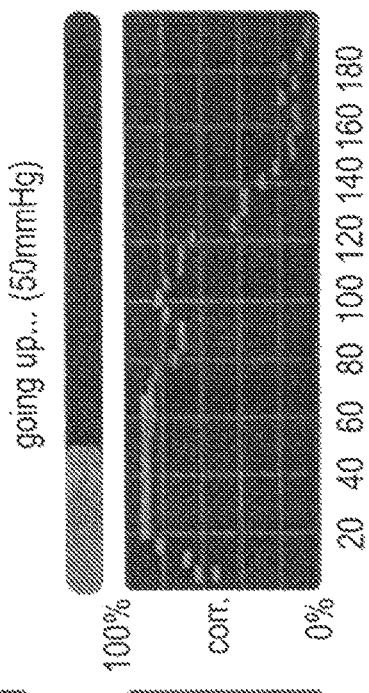
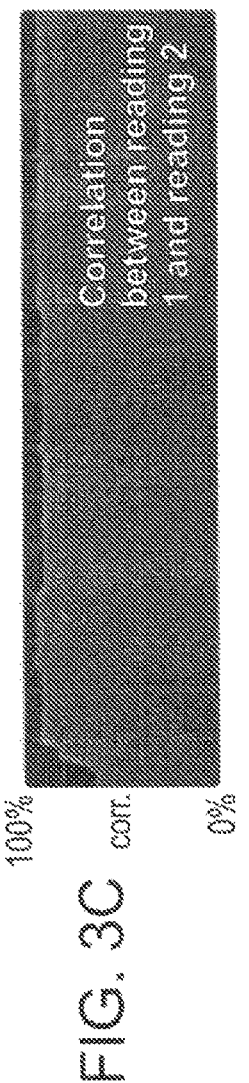
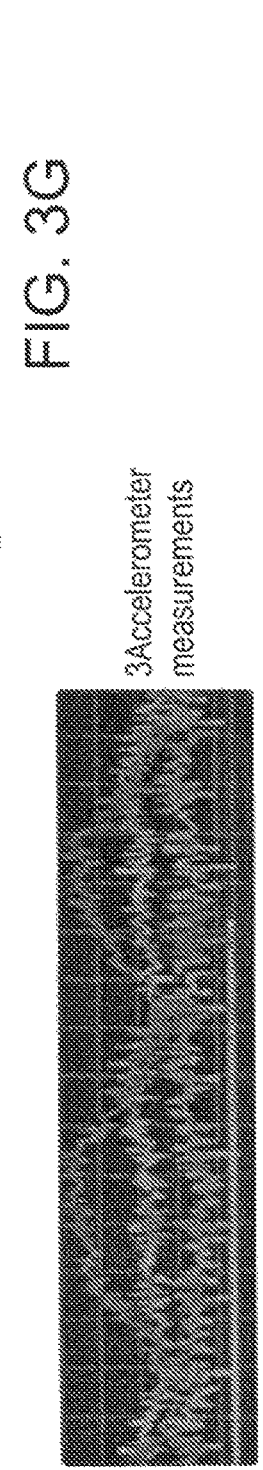

VITAL SIGN MONITORING APPARATUSES AND METHODS OF USING SAME

RELATED APPLICATIONS AND PRIORITY

This application claims priority under Article 8(1) PCT to U.S. Pat. App. No. 62/120,545 filed on Feb. 25, 2015 and U.S. Pat. App. No. 62/136,741 filed on Mar. 23, 2015, the disclosures of which are incorporated herein by reference.

TECHNICAL FIELD AND BACKGROUND

Disclosed embodiments relate to the health care industry and, more particularly, but not exclusively, to a system and apparatus for monitoring and/or measuring vital signs.

In general, known devices may be unsuitable to provide sufficient accurate and robust indication as to whether and when a patient's health condition is expected to deteriorate. This is true not only for patients whose vital signs parameters are collected only periodically, for example, every few hours in the hospital or through home-care, but may also hold for patients hospitalized in Intensive Care Units (ICUs) where their vital signs may be constantly monitored.

SUMMARY

Aspects of disclosed embodiments relate to a system for vital sign measuring of a patient.

According to example 1, the system comprises a first sensor removably attachable with a first body portion of the patient and configured to measure, when in operable position, a vital sign of the patient; at least one additional sensor removably attachable with a second body portion of the patient and configured to measure, when in operable position, a vital sign of the patient; and a processor configured to provide data descriptive of a level of correspondence between measurements of the vital signs provided by the first sensor and the at least one additional sensor.

Example 2 includes the subject matter of example 1 and, optionally, wherein the first sensor comprises a first plethysmograph removably attached to a first finger of a patient; wherein the at least one additional sensor comprises a second plethysmograph removably attached to a second finger of the patient; the system further comprising a pressure cuff removably between the first plethysmograph and the ipsilateral palm of the patient; and an inflation device configured to inflate the pressure cuff; wherein the processor is configured to provide data descriptive of a level of correspondence between signals received from the first and second plethysmographs.

Example 3 includes the subject matter of any of examples 1 to 3 and, optionally, wherein the at least one additional sensor is at least one of an accelerometer, a thermometer, a sound meter or a digital pressure sensor or a combination thereof.

Example 4 includes the subject matter of any of the preceding examples and, optionally, wherein the processor is further configured to perform at least one of commanding the inflation device, sending to and receiving signals from the sensor and the at least one additional sensor, sending to and receiving signals from the pressure cuff, and correcting or weighting received signals from the first sensor and the at least one additional sensor.

Example 5 includes the subject matter of any of the preceding examples and, optionally, wherein the processor is located remotely from the patient.

Example 6 includes the subject matter of any of the preceding examples and, optionally, wherein the signals in the system are communicated wirelessly.

Example 7 includes the subject matter of any of the preceding examples and, optionally, wherein the system is configured to be wearable by the patient.

Example 8 includes the subject matter of any of the preceding examples and, optionally, wherein at least a portion of the system is configured to be wearable by an attending medical professional.

Example 9 includes the subject matter of any of the preceding examples and, optionally, further comprising a deflation device for deflating the pressure cuff in a controllable manner.

Example 10 includes the subject matter of any of the preceding examples and, optionally, wherein the processor determines from received signals at least one of systolic blood pressure, diastolic blood pressure, mean arterial pressure, pulse rate, breathing rate, breathing pattern, saturation level, motor function, temperature and, cognitive ability of the patient.

Example 11 includes the subject matter of any of the preceding examples and, optionally, wherein the level of correspondence is expressed as correlation.

Example 12 includes the subject matter of example 1, where the processor comprises at least one of a motor controller, a micro controller and an analog front-end.

Example 13 includes the subject matter of example 2, where the inflation device comprises at least one of a pump and a valve.

Example 14 includes a method for vital sign measuring, comprising: removably attaching a first sensor to be in an operable position to a first body portion of the patient for measuring a vital sign of the patient; removably attaching at least one additional sensor to be in an operable position to a second body portion of the patient for measuring a vital sign of the patient; and determining a level of correspondence between a first signal from the first sensor and at least one additional signal received respective of the at least one additional sensor.

Example 15 includes the subject matter of example 14 and, optionally, wherein the first sensor comprises a first plethysmograph removably attachable to a first finger of a patient; wherein the at least one additional sensor comprises a second plethysmograph removably attachable to a second finger of the patient; wherein the method further comprises: inflating a pressure cuff attached to the first finger between the first plethysmograph and a respective ipsilateral palm of the patient; determining a level of correspondence between a first signal from the first plethysmograph and a second signal from the second plethysmograph; and determining the systolic blood pressure of the patient based on a change in the level of correspondence.

Example 16 includes the subject matter of example 14 and, optionally, wherein the at least one additional sensor comprises an accelerometer for detecting motion of the at least a portion of the patient.

Example 17 includes the subject matter of example 14 and, optionally, wherein the at least one additional sensor comprises a thermometer for assessing vasodilation in response to warming of the at least a portion of the patient.

Example 18 includes the subject matter of example 14 and, optionally, wherein the at least additional sensor comprises a sound meter for measuring sound level of the patient.

Example 19 includes the subject matter of example 14 and, optionally, wherein the at least one additional sensor is removably attached to a second body portion to detect additional information relating to vital signs of the patient to correct data descriptive of signals received from the first sensor.

Example 20 includes the subject matter of any of the examples 14 to 19 and, optionally, further comprises determining the diastolic blood pressure.

Example 21 includes the subject matter of example 19 and, optionally, wherein the at least one additional sensor is an accelerometer.

Example 22 includes the subject matter of any of the examples 14 to 21 and, optionally, further comprising using an oscillometric method for determining systolic blood pressure, diastolic blood pressure or both.

Example 23 includes the subject matter of example 15, further comprising repeating inflating and deflating the pressure cuff a plurality of times to determine diastolic blood pressure.

Example 24 includes the subject matter of example 23, where diastolic blood pressure is determined to be where a jump in the first signal occurs.

Example 25 comprises a method for vital sign measuring, including removably attaching at least one accelerometer to a first hand of a patient; placing the first hand of the patient on the patient's abdomen or chest; and measuring motion detected by the at least one accelerometer to determine at least one of a breathing pattern and breathing rate of the patient.

Example 26 includes the subject matter of example 25 and, optionally, further comprising removably attaching at least a second accelerometer to a second hand of the patient and having the patient place the second hand in a different location on the patient's body than the first hand to determine a breathing pattern of the patient.

Example 27 includes the subject matter of example 25 and, optionally, wherein the breathing pattern comprises a breathing rate.

Example 28 comprises a wearable system for vital sign measuring including an at least partial glove garment, comprising a first finger sleeve and a second finger sleeve and a palm portion; a first plethysmograph coupled with the first finger sleeve; a second plethysmograph coupled with the second finger sleeve; a pressure cuff coupled with the first finger sleeve between the first plethysmograph and the glove's palm portion; and an inflation device coupled with the garment and configured to inflate the pressure cuff.

Example 29 includes the subject matter of example 27 and, optionally, further comprising a processor configured to determine a level of correspondence of signals received from the first and second plethysmographs coupled with the first and second finger sleeves, respectively, or the harness.

Example 30 includes a system for determining a mental state of a person, the system comprising at least one accelerometer; and a processor coupled with the at least one accelerometer, wherein the processor is operative to determine a mental state of the patient based on data descriptive of signals received from the accelerometer.

Example 31 includes a method of gauging vital sign parameters, comprising monitoring one or more vital signs of a patient using a wearable vital sign measuring system during an activity.

Example 32 includes the subject matter of example 31, where a vital sign is at least one of systolic blood pressure, diastolic blood pressure, mean arterial pressure, pulse rate, breathing rate, breathing pattern, hemoglobin oxygen saturation level, motor function, temperature or cognitive ability of the patient.

Example 33 includes the subject matter of example 31 or example 32, where an activity is at least one of working, performing physical exercise, resting or sleeping.

Example 34 includes the subject matter of any of the examples 31 to 33, and further includes storing monitored vital signs of the patient during the activity.

Example 35 includes the subject matter of any of the examples 31 to 34, and further includes establishing whether a value of a vital sign parameter corresponds to an expected value, taking into account the current activity of the patient monitored.

Example 36 includes the subject matter of example 34, and further includes providing an output indicative of at least one of a forecast or suggestion of one or more treatment options based on data descriptive of stored vital sign values.

Example 37 includes a method of assessing patient ability, comprising: instructing the patient to perform a reference movement; and, recording, using a wearable vital sign measuring system, a first patient movement data set descriptive of the movement performed by the patient when attempting to copy the reference movement.

Example 38 includes the subject matter of example 37, and further includes comprising recording a second patient movement data set descriptive of the movement performed by the patient when attempting to copy the reference movement, and comparing the second patient movement data set to the first patient movement data set.

Unless otherwise defined, all technical and/or scientific terms used herein have the same meaning as commonly understood by one of ordinary skill in the art to which the disclosed embodiments pertain. Although methods and materials similar or equivalent to those described herein can be used in the practice or testing of embodiments of the invention, exemplary methods and/or materials are described below. In case of conflict, the patent specification, including definitions, will control.

In addition, the materials, methods, and examples are illustrative only and are not intended to be necessarily limiting.

Implementation of the method and/or system of embodiments of the disclosed embodiments can involve performing or completing selected tasks manually, automatically, or a combination thereof. Moreover, according to actual instrumentation and equipment of embodiments of the method and/or system of the invention, several selected tasks could be implemented by hardware, by software or by firmware or by any combination thereof, using for instance an operating system.

For example, hardware for performing selected tasks according to disclosed embodiments may include a chip and/or a circuit. As software, selected tasks according to disclosed embodiments could be implemented as a plurality of software instructions being executed by a computer using any suitable operating system. In an embodiment, one or more tasks that may be associated with embodiments of the method and/or system as described herein may be performed by a processor, such as a computing platform for executing the plurality of instructions. Optionally, the processor includes and/or is operatively coupled with a volatile memory for storing instructions and/or data, and/or a non-volatile storage, for example, a magnetic hard-disk and/or removable media, for storing instructions and/or data. Optionally, a network connection is provided as well. An output device, for example, a display, and/or a user input device, for example, a keyboard and/or mouse are optionally provided as well.

This summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE SEVERAL VIEWS OF THE DRAWINGS

Some embodiments are herein described, by way of example only, with reference to the accompanying drawings. With specific reference now to the drawings in detail, it is stressed that the particulars shown are by way of example, and not necessarily to scale, and are for purposes of illustrative discussion of the embodiments. In this regard, the description taken with the drawings makes apparent to those skilled in the art how embodiments may be practiced.

In the drawings:

FIG. 3A is a graph of detected plethysmograph readings from a first finger (with a pressure cuff) and a second finger over time using a first protocol, in accordance with an embodiment;

FIG. 3B is a graph showing the pressure within the pressure cuff over time, where the time axis corresponds to the time axis of FIG. 3A, in accordance with an embodiment;

FIG. 3C is a graph showing a correlation between plethysmograph readings from the first finger and the second finger where the time axis corresponds to the time axis of FIG. 3A, in accordance with an embodiment;

FIG. 3D is a graph of a triaxial accelerometer reading, the accelerometer applied on one of the patient's hand which is placed on his/her chest, where the time corresponds to the time of FIG. 3A, in accordance with an embodiment;

FIG. 3E is a graph of the alternating component of the plethysmograph signal for each of the fingers, in accordance with an embodiment;

FIG. 3F is a bar showing the pressure buildup in the pressure cuff, in accordance with an embodiment;

FIG. 3G is a histogram showing the correlation between the plethysmograph correlation (Y axis) and pressure level of the pressure cuff (X axis), in accordance with an embodiment;

DETAILED DESCRIPTION

Figure 1:
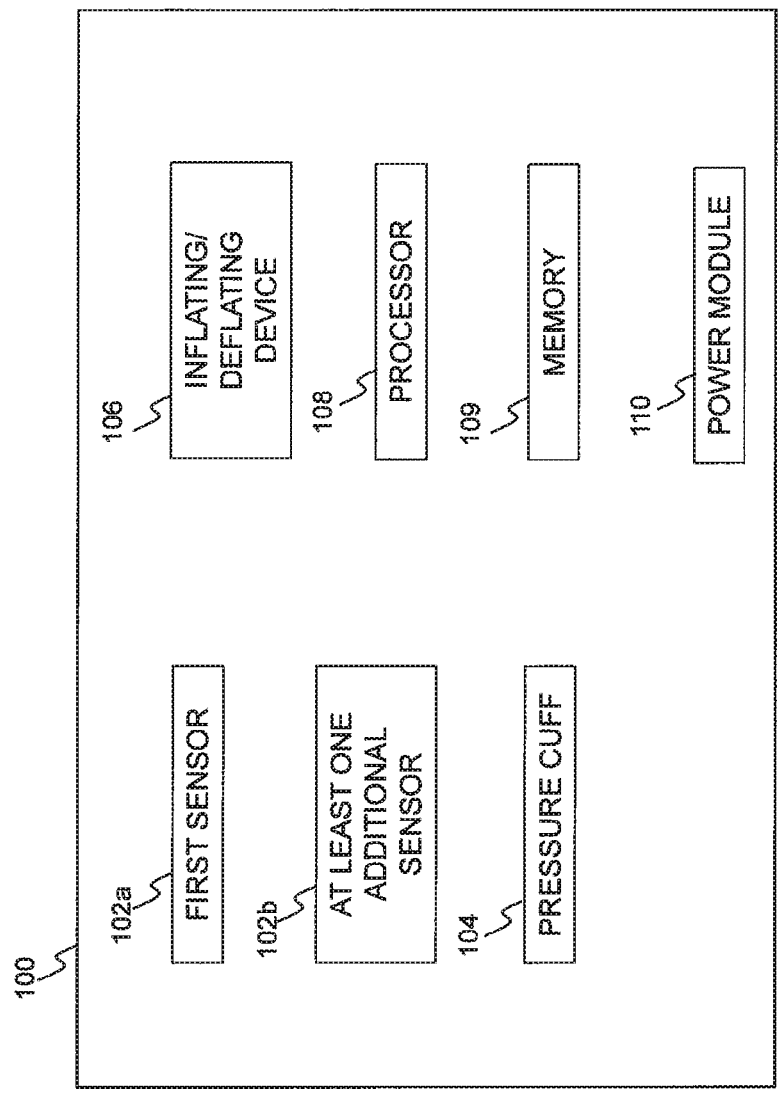
FIG. 1 is a schematic block diagram of a vital sign measuring system, in accordance with an embodiment.

Disclosed embodiments relate to the health care industry and, more particularly, but not exclusively, to a system and apparatus for monitoring and/or measuring vital signs.

The disclosed embodiments are not necessarily limited in its application to the details of construction and the arrangement of the components and/or methods set forth in the following description and/or illustrated in the drawings and/or the Examples. The embodiments are capable of being practiced and/or carried out in various ways.

In the health care industry, current oscillometric methods are relatively accurate in measuring Mean Arterial Pressure (MAP) but much less accurate in determining systolic/diastolic pressure. In practice, when deflating a blood pressure measurement cuff, one first "passes" the systolic pressure. However, the signal indicative of the systolic pressure is spread out over a relatively large pressure range and is therefore inaccurate.

Further deflation of the cuff results in a pressure level where the cuff resonates, which is conventionally interpreted to be at the MAP.

Additionally, because the diastolic pressure is calculated based on a formula from the determined systolic blood pressure and/or mean arterial pressure, it is also subject to inaccuracy as a result of shortcomings that are associated with the determination of the systolic blood pressure and employment of a mathematical formula rather than direct measurement. In addition, the algorithms that are employed to extract/derive the systolic and/or diastolic blood pressure vary from company to company and not standardized.

Generally, a system is provided which is configured to accurately, quickly and/or non-invasively measure and/or monitor at least one patient vital sign, for example, systolic blood pressure, diastolic blood pressure, mean arterial pressure, pulse rate, breathing rate, breathing pattern, hemoglobin oxygen saturation level, motor function, temperature and/or, cognitive ability, in various clinical scenarios, including for emergency medicine and/or acute care scenarios. In some embodiments, multiple vital signs are measured using the same system using different types of sensors and/or modalities, enabling better accuracy and/or inter-parameter physiologic "reality checks" and/or redundancy and/or synergistic noise reduction. In some embodiments, the system is configured with a modular design, described in more detail below.

In some embodiments, by employing wearable device, the system is operative to monitor one or more vital signs of the patient who may, at the same time, engage in everyday activities including, for instance, working, performing physical exercise, resting or sleeping. It is noted that the values of vital sign parameters may be affected by the patient's activity. For example, when exercising, the patient's heart rate may increase compared to the heart rate when in a resting state. As an additional example, the patient's blood pressure during sleep may be reduced compared to waking blood pressure. In some embodiments, the system may be configured to establish whether a value of a vital sign parameter corresponds to an expected value, taking into account the current activity of the patient monitored.

The system is further operative to provide long-term storage of data descriptive of values of measured vital sign parameters. The system may for example be operative to store such data descriptive of vital signs and display the history of the values of vital signs monitored (e.g., a historical trend) for hours (e.g., 24 hours at least); days (e.g., 7 days at least), weeks (e.g., 4 weeks at least), months (e.g., 6 months at least) or years (e.g., 2 years at least) and, optionally, provide an output indicative of a forecast and/or suggestion one or more treatment options based on the data descriptive of past values. Such output may additionally or alternatively comprise raising an alarm, initiating a call to a caregiver, cause more frequent measurements, and the like.

The system may be operative to provide outputs of values of monitored vital signs parameters meeting medical grade.

The system's outputs may thus meet the requirements set by a "Gold Standard", which may refer to any standard that may meet regulatory requirements and/or that is widely or internationally accepted by the medical and/or scientific community as a benchmark.

The assessment of measurement accuracy of blood pressure for a given BP device for example can be determined according to the standard proposed by the British Hypertension Society (BHS) and the US Association for the Advancement of Medical Instrumentation (AAMI). For the standard proposed by the BHS, grading criteria are defined as cumulative percentage of readings falling within a certain BP range.

According to some embodiments of the devices, systems and methods disclosed herein achieve Grade A of available Grades A to Grade D according to the BHS-defined standard, i.e., at least 60% of the systolic and diastolic measurements performed fall within the gold standard measurement, +/−5 mmHg.

Referring now to the drawings, FIG. 1 is a schematic block diagram of a vital sign measuring system 100, in accordance with an embodiment. The system 100 comprises in an embodiment a first sensor 102a and at least one additional sensor 102b. The first sensor 102a may be embodied by a first plethysmograph and the at least one additional sensor 102b may be embodied by a second plethysmograph. The first and second plethysmographs may be implemented as dual wavelength photoplethysmographs. Optionally, each of the plethysmographs 102a/102b is removably and operably attachable (e.g. to the patient's fingers). For example first plethysmograph 102a may be engaged with the index finger and the second plethysmograph 102b with the middle finger of the same (ipsilateral) hand. Alternative configurations may be conceived. For instance, first plethysmograph 102a may be engaged with a finger of a first hand and second plethysmograph 102b may be engaged with a finger of the patient's other hand. The fingers may be in some embodiments contralateral.

In an embodiment, a pressure cuff 104 for applying an occluding pressure on the finger is applied on one of the fingers between the palm and the plethysmographs on that finger. In an embodiment, an inflating/deflating device 106 for inflation/deflation of the pressure cuff 104 as well as a memory 109 and a power module 110 for enabling the powering of the various components of system 100 may also be provided. The inflating/deflating device 106 may for example be embodied by a portable (e.g., wearable) electronically and/or mechanically operable device, which may be lightweight. The inflating/deflating device may for example include a controllable pump or a syringe that operably coupled with a valve for enabling control of flow rate during deflation for example of the pressure cuff 104.

In an embodiment, the at least one additional sensor 102b may further comprise a digital pressure sensor and/or at least one accelerometer and/or a sound meter and/or a temperature sensor, and/or a sensor operative to provide an indication about arterial (e.g., peripheral) tone and, based on the indication, provide an output indicative of a change of a physical condition of the patient such, for example, a sleep state and/or condition (e.g. sleep apnea, onset of REM sleep state) and/or of heart function or condition (e.g., myocardial ischemia) for example.

In some embodiments, a wearable pressure sensor may be operatively coupled with the cuff 104 for measuring the pressure in the cuff and for providing the processor with data descriptive of the measured pressure.

In an embodiment, at least one additional sensor 102b (in addition to the second plethysmograph) is wearable and/or is positioned on the patient to function synergistically with the first and second plethysmographs, for example at least one accelerometer is located in the vicinity of the first and/or second plethysmograph to assist with correction of the readings from the nearby plethysmograph based on sensed motion of the patient from the accelerometer. In an embodiment, a sound meter may engage a body part of the patient in an operable position for measuring sound level in a sleep study. In an embodiment, a temperature sensor, in operable position, may be used for assessing vasodilation in response to warming.

In some embodiments, additional sensor(s) 102b may also include at least one accelerometer that can be operatively coupled with a part (e.g., finger) of one of the patient hands. The patient may place the hand with the accelerometer coupled thereto onto his/her chest or abdomen so that the accelerometer can sense changes in movements of the chest or the abdomen. These sensed changes can then be used by system 100 for determining the patient's breathing pattern, which may for instance include a breathing rate. In some embodiments, the at least one additional sensor 102b may include a second accelerometer that can be operatively coupled with a part of the patient's other hand. The two accelerometers may for example be used for substantially simultaneous sensing of movements of the chest and the abdomen for example by placing one of the patient's hands on his/her chest and the other hand on his/her abdomen.

In an embodiment, at least one accelerometer is used to assess patient capability, mental or physical or both. For example, while removably attached to at least one accelerometer of the system the patient is requested to perform a certain motion or series of motions which the accelerometer measures. The measured motion is compared to an expected performance value in order to gauge the condition of the patient.

In some embodiments, a patient may be asked or trained to perform (e.g., mimic) a given reference movement, which may herein also include a sequence of movements. The system may record first data ("first patient movement-data") descriptive of the movement performed by the patient when attempting to copy the given reference movement, using one or more sensors (e.g., accelerometers). A patient's later performed movement may be identified by the system as corresponding to the given reference movement. Second patient-movement-data descriptive of such later movement performed by the patient may be compared with the first patient-movement-data and analyzed. In some embodiments, the patient may attempt to perform the given reference movement responsive to being cued to do so, e.g., automatically by the system or by a medical professional (e.g., a care giver). The medical professional may communicate with the patient over a communication network (not shown).

The system 100 may comprise a processor/controller 108. In some embodiments, the processor 108 may execute instructions stored in memory 109 resulting in performing at least one of the following operations: receiving data from the at least one additional sensor 102b; controlling the inflating/deflating device 106; handling communication/alerts between system 100 components, the user and/or the patient; schedules "data collection" depending on the care scenario, for example different patients in different scenarios may need frequency of measurements and/or different alarm limits (e.g. for a critically injured soldier in the field or for a patient in an evacuation helicopter, a continuous or almost continuous measurement of at least some of the vital signs is warranted, whereas for a stable, ambulating, and/or low risk patient in a ward in the hospital perhaps only once every 6 hours); and/or handles signal processing. In an embodiment, communication within the system 100 and/or to and/or from the system (e.g. to the patient, attending medical professional, user of the system, etc.) can be wired and/or wireless. In some embodiments, processor 108 may be embodied by an on-board processor 108. The system 100 may be configured to be in operative communication with a communications network, for example the Internet, local hospital servers or remotely located servers, the "cloud", and the like. Some processing and/or data storage tasks are performed remotely on remote processors and/or databases. In some embodiments, the system 100 is configured for communications based on the anticipated use of the system 100. For example, a system 100 configured for battlefield and/or ambulatory use may have a more robust wireless communications capability (e.g. more bandwidth) than a system 100 in a hospital use scenario.

In an embodiment, at least one component of the system 100, for example the processor 108, executes a computer software program. In an embodiment, a user interface is provided for controlling and/or setting behavior or performance of the system 100. The system may thus comprise a computer-program product. For example, varying sensitivity of the system, setting alarm thresholds for vital signs, and/or enabling warnings for poor signal quality as determined for example by a signal-to-noise ratio and/or any other quality-related threshold (e.g. to and/or from sensors in the system 100, to and/or from remote components of the system 100, to and/or from a communications network) can be controlled through the user interface.

In some embodiments, the processor 108 handles plethysmograph related tasks including processing heart rate, determining a level of correspondence (e.g., correlation) between plethysmograph readings, oxygen saturation, pulsatile ("AC")/constant ("DC") component, determination of breath rate, heart rate and/or volume changes, depth of anesthesia, and/or vasodilatation/constriction (temperature, medication, assessment of shock).

While embodiments exemplify the use of correlation for determining a level of correspondence, this should by no means to be construed as limiting.

In some embodiments, the processor 108 handles pressure sensor related tasks including determining systolic blood pressure (by return of a plethysmograph signal) and/or systolic and diastolic blood pressure (using an oscillometric method).

In some embodiments, as already indicated herein above, the processor 108 handles accelerometer related tasks including ascertaining respiratory rate (breaths per minute) when hand placed on thorax/abdomen, and/or motion detection for noise-reduction from at least one sensor.

In some embodiments, the processor 108 handles integration of the received sensor data including noise reduction, including dynamic band pass filters based on motion detection, reduction of "noise" caused by other physiologic processes (e.g. breath rate on heart rate), determination of value of a vital sign after analyzing modalities (e.g. which systolic, diastolic and/or mean arterial blood pressure to display: whether from an oscillometric calculation or from a return of a plethysmograph signal pressure or a synthesis of both; and/or a respiratory rate from a plethysmography waveform and/or from at least one accelerometer).

In an embodiment, all components of the system 100 described herein are wearable and/or are human transportable. For example, in an embodiment various components of the system 100, the various sensors such as the plethysmographs, the pressure cuff, the inflation/deflation device, the memory, power module and/or the processor and/or, are provided together in a hand-wearable glove or partial glove whereby all of the components can be removably attached or placed onto the patient, in the correct locations on the patient and/or relative to each other, relatively quickly and conveniently. Optionally, at least a portion of the glove is flexible, for example because the pressure cuff is integral to the glove and the cuff portion of the glove reversibly stretches in response to inflation of the cuff. In some embodiments, at least a portion of the system, for example the processor, is located in a bag or pack or on a harness or belt to be worn by the patient or the attending medical professional or both.

In some embodiments, the system 100 is modular. For example, all of the components are integrated into a single unit. In an embodiment, the system 100 is divided between the patient and an attending medical professional, for example at least one of the plethysmographs, the pressure cuff and the additional sensors are positioned on the patient, while the processor is located on the attending medical professional. In another embodiment, at least one of the plethysmographs, the pressure cuff and the additional sensors are positioned on the patient and the processor is located remotely from the patient (i.e. via a communications network such as the Internet).

Figure 4:
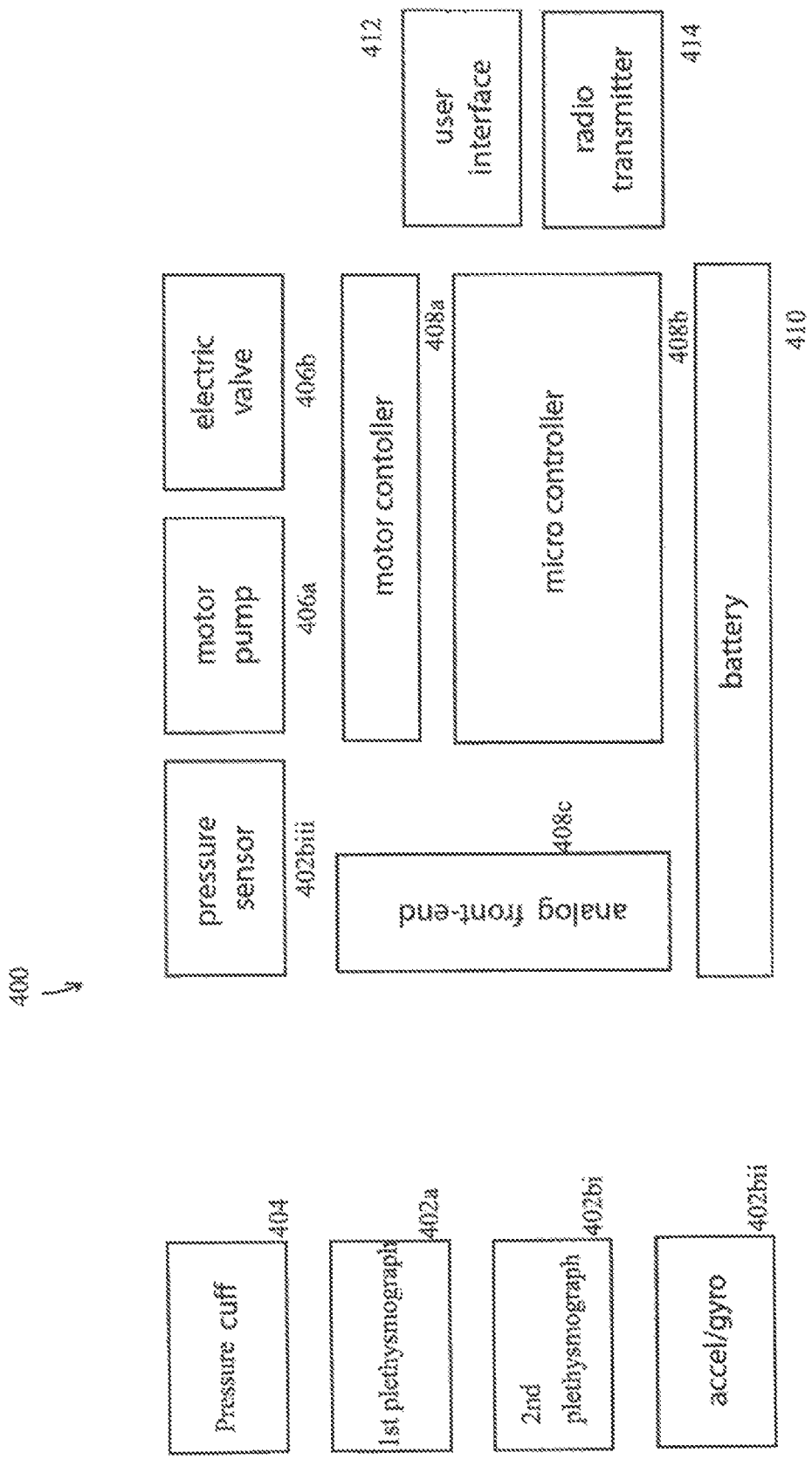
FIG. 4 is a schematic block diagram of an alternative vital sign measuring system, in accordance with an embodiment; and, FIGS. 5A-5C are signal outputs of detected plethysmograph readings from a first finger (with a pressure cuff) and a second finger over time using the second protocol, where each of FIG. 5A-5C represents a discrete progression through the second protocol, in accordance with an embodiment of the invention.

FIG. 4 is a schematic block diagram of an alternative vital sign measuring system 400, in accordance with an embodiment of the invention. Some of the system 400 components are the same as, or similar to, equivalent components in system 100. Reference numbers for system 400 follow the reference numbers for system 100 (e.g. pressure cuff 104 is similar to or is actually the same as pressure cuff 404, first sensor 102a is similar to or is actually the same as first plethysmograph 402a), although some components are not present and/or specifically shown in each diagram. Optionally, some of the components of system 400 are subsumed by more general components described in system 100. Optionally, some of the components of system 400 are in addition to components described in system 400. Optionally, system 100 has components not described with respect to system 400. For the sake of brevity, exemplary distinctions between system 100 and system 400 are described.

In an embodiment of the invention, system 400 inflating/deflating device may for example include a controllable pump 406a or a syringe that is operably coupled with a valve 406b for enabling control of flow rate during deflation for example of the pressure cuff 404.

In an embodiment, the at least one additional sensor 402b may further comprise a digital pressure sensor 402biii and/or at least one accelerometer 402bii and/or any of the other sensor types referenced herein, for example.

In an embodiment of the invention, processor 108 of system 100 has a functional equivalent in system 400 which includes at least one of a motor controller 408a, a micro controller 408b, and an analog front-end 408c. In an embodiment of the invention, motor controller 408a optionally controls the pump 406a. In an embodiment of the invention, the analog front-end 408c is used to provide a configurable and/or flexible electronics functional block, to interface the sensors 402a, 402b with the motor controller 408a and/or the micro controller 408b.

In an embodiment of the invention, a user interface 412 is provided to facilitate user interaction with system 400.

Optionally, a radio transmitter 414 and/or other communications equipment is provided to system to enhance connectivity.

Figure 2:
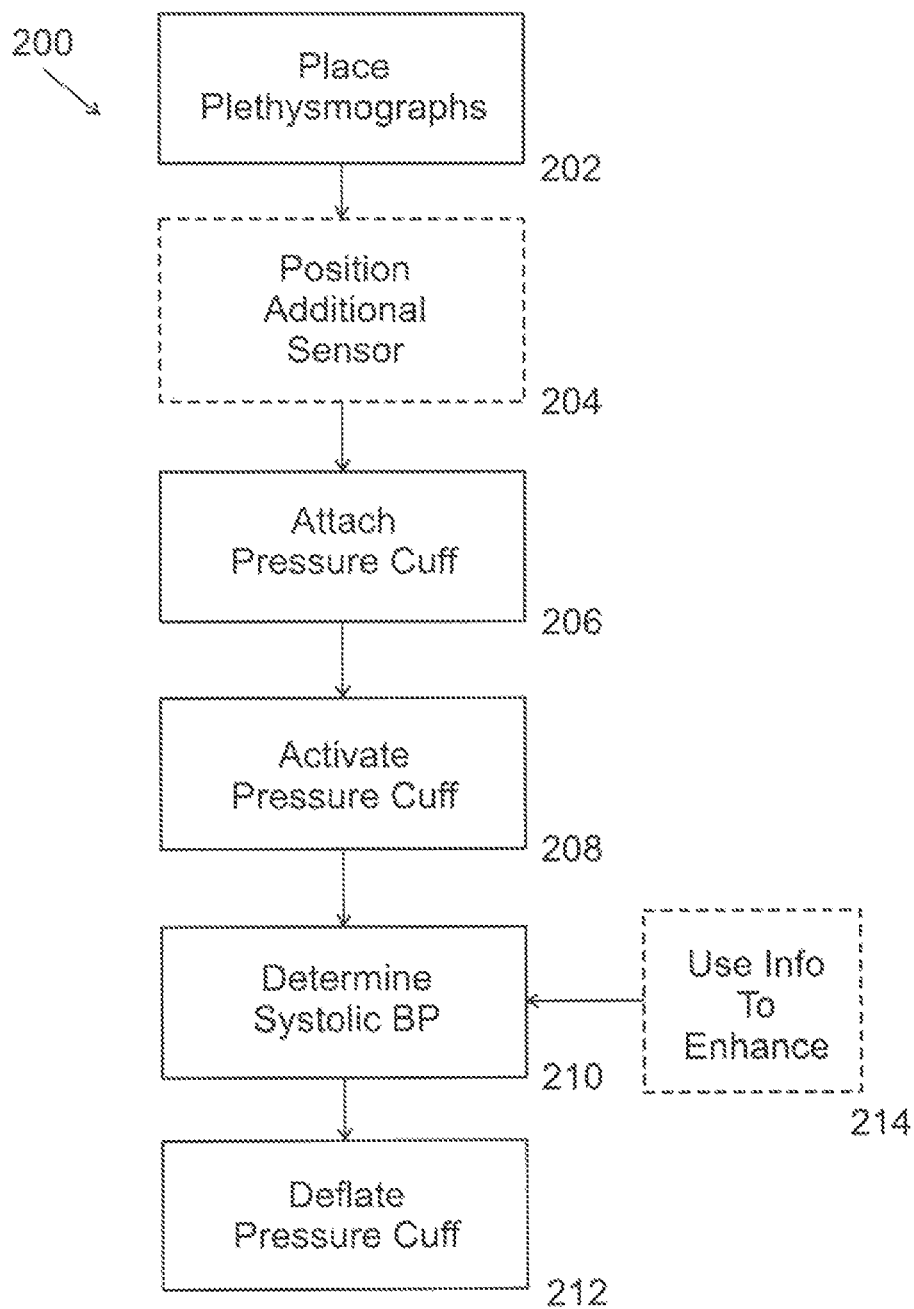
FIG. 2 is a flowchart of a method of using a vital sign measuring system, in accordance with an embodiment.

It should be understood that either system 100, 400 is useable with the first protocol described herein with respect to FIGS. 2 and 3A-3G and the second protocol described herein with respect to FIGS. 2 and 5.

FIG. 2 is a flowchart 200 of a method of using a vital sign measuring system 100, 400, in accordance with an exemplary embodiment, the method is a plethysmograph correlation-based method that provides a more "direct" or straightforward approach of determining, at the very least, systolic blood pressure compared to prior, conventional methods of determining systolic blood pressure. The methods described herein more quickly determine the systolic blood pressure, requiring less time and/or caution when deflating the pressure cuff than is currently practiced in order to avoid missing the threshold of conventional methods indicative of the systolic blood pressure.

In an embodiment, a patient is removably connected to the system 100, 400 by placing (202) a first plethysmograph 102a on a patient's first finger and a second plethysmograph 102b on a patient's second finger. In an embodiment of the invention, at least another sensor 102b, such as those described herein are positioned (204) on the patient, for example at least one accelerometer. In an embodiment, a pressure cuff 104 is removably attached (206) to the first or second finger, between the patient's palm and the plethysmograph.

Systolic blood pressure is determined (208), in an embodiment, by determining correlation between data descriptive of signals received from the first and second plethysmographs 102a/102b. Various operational parameters and/or patient driven measurements are displayed by the system 100 to at least a user of the system 100, 400, for example as are shown in FIGS. 3A-3G. In an embodiment, a correlation is determined over a window of time during which signals from the plethysmographs 102a/102b are received by the system 100, 400. Optionally, the window is about 1 second.

Optionally, the window is shorter or longer in time. In an at rest condition of the patient, the correlation between the signal from the first plethysmograph 102a and the second plethysmograph 102b should be close to 1, that is they should be very close to the same. In an embodiment, when the pressure cuff 104 is activated (210) to inflate and restricts the blood flow in the finger on which it is attached (206), the correlation will drop dramatically since the AC component of the signal in the compressed finger will be nearly 0. In an embodiment, the system 100, 400 is set to determine the systolic blood pressure when the correlation drops to a level below a certain correlation threshold, e.g., relatively precipitously. See for example see FIG. 3G which shows correlation (100% on the y-axis=a correlation ratio of 1) versus pressure cuff inflated pressure (where a relatively precipitous drop occurs at approximately 125 mm Hg and thus the systolic blood pressure is determined to be about 125 mmHg). For example, the correlation threshold could be set to 0.85, optionally over a window of time, such as the 1 second described above. It should be understood that these settings (correlation ratio and/or window of time) could be set at almost any number and those offered above are by way of example only and are optionally variable based depending further clinical testing and/or comparison to "Gold standard" blood pressure measurements.

Eventually, the pressure cuff 104 is deflated (212), restoring full blood flow in the finger and at a rate sufficiently slow to detect minute changes in correlation between data readings received from the two plethysmographs 102a/102b. Based on such changes during deflation of the pressure cuff, blood pressure values such as systolic blood pressure may be determined.

In some embodiments, systolic BP is determined during deflation (212) by monitoring a specific change in increase of correlation between data received from the two plethysmographs 102a/102b and/or using the oscillometric method.

In some embodiments, the diastolic blood pressure may be determined during deflation (212) using the oscillometric method, such as described elsewhere herein.

In practice, the method or protocol varies, optionally dynamically, depending on the patient and/or the treatment scenario. For example, the process of inflation and/or deflation of the pressure cuff 104, and the resultant change in correlation, are not typically instantaneous and/or may vary slightly from patient to patient. As another example, the length of the window of time may be shorter for a patient with a faster pulse rate (more pulses per minute means more amplitude peaks and signal changes in a given time frame, yielding a higher signal to noise ratio when comparing signals from the two fingers). As a result, the systolic blood pressure could be a pressure near the beginning, near the middle or near the end of the window of time. In an embodiment, the blood pressure chosen as the systolic blood pressure and/or the length of the window of time are decided as a result of fine-tuning the system 100 with high fidelity sensors compared against the conventional gold standard.

Accordingly, the devices and system disclosed herein may meet medical grade requirements.

In some embodiments, the diastolic pressure is determined using a method similar or related to how the systolic blood pressure is determined. Namely, after a quick inflation and then gradual deflation of the pressure cuff scenario, the amplitude of the AC part of the plethysmograph reading in the cuffed finger slowly rises from return of pulsation (systolic BP) to a constant level, it is believed that the cuff pressure from which constant pulsations are seen from the plethysmograph readings is the diastolic blood pressure. In an embodiment, the diastolic blood pressure reading is confirmed using at least one additional sensor 102b which provides information on both the AC and DC components of the plethysmograph reading(s).

In some embodiments, diastolic blood pressure is determined using a second protocol during deflation (212) from a higher pressure to a lower pressure where a jump/transition (see an exemplary jump 510 in FIG. 5B) in the plethysmograph reading exceeds a predefined amount (or delta), where a higher pressure immediately at the jump/transition is determined to be the diastolic blood pressure. It should be noted that inflating (208) and deflating (212) the plethysmograph entirely beneath the diastolic blood pressure will not register a jump/transition sufficient enough to determine a diastolic blood pressure, while inflating (208) to a level above the diastolic blood pressure will cause a "stutter" or jump in the plethysmograph during subsequent deflation (212), which allows for the determination of diastolic blood pressure (which happens at the stutter).

In some embodiments of the invention, a repetitive, but incrementally increasing in inflation pressure, is used in the second protocol to measure diastolic blood pressure. For example, at least the actions of inflating/activating (208) the pressure cuff and then deflating (212) the pressure cuff are repeated at least two or three times, where the inflation pressure of the pressure cuff increases at least slightly each successive cycle. After at least two or three repeated cycles of inflating (208) and deflating (212) the recorded pressure during deflation (212) where there is a sudden detected change in the behavior of the plethysmograph is designated to be the diastolic blood pressure.

Figure 5A:
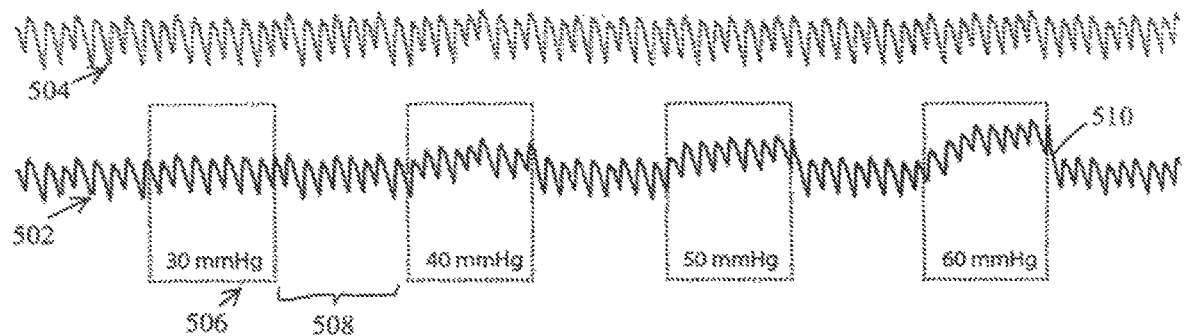
Figure 5B:
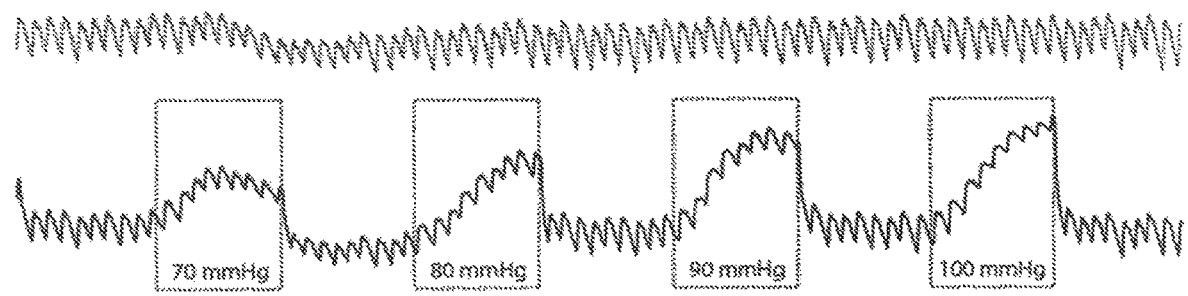
Figure 5C:
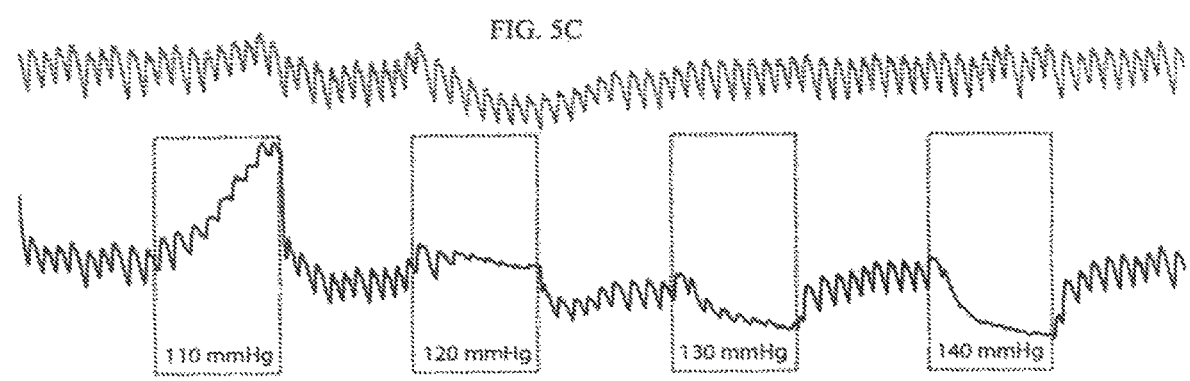

FIGS. 5A-5C are signal outputs of detected plethysmograph readings from a first finger (with a pressure cuff) and a second finger over time using the second protocol, where each of FIG. 5A-5C represents a discrete progression through the second protocol, in accordance with an embodiment of the invention. The solid black line 502 in each Figure corresponds to the plethysmograph signal recorded from the first plethysmograph 402a, while the dotted line 504 above the solid black line 502 in each Figure corresponds to the plethysmograph signal recorded simultaneously from the second plethysmograph 402bi on the control finger (without the pressure cuff).

In an embodiment of the invention, each one of FIG. 5A, FIG. 5B and FIG. 5C is equivalent to 90 sec of recording where the y-axis in each Figure represents the amplitude of the plethysmograph 402a, 402bi signals (at an arbitrary scale, yet identical in all Figures), the dashed-rectangles indicate intervals 506 of inflation in the pressure cuff 404 (each at a constant pressure indicated at mmHg units), and at the end of each interval, the pressure at cuff 404 is released to 0 mmHg. In an embodiment of the invention, two main changes in the plethysmograph signal are identified as a function of cuff pressure: 1) the baseline of the signal (the DC component) is affected (increased at ~60-110 mmHg, and decreased at 130 mmHg and above); and, 2) the amplitude of the pulsation (the AC component) decreases as the pressure increases. In FIG. 5A, for example, diastolic blood pressure could be said to be at 60 mmHg. In FIG. 5C, it could be 120 mmHg.

In an embodiment of the invention, additional inflating (208) in the second protocol after the initial inflation (208) is only performed after the initial deflating (212) is complete, allowing fluid that might have traversed from the intravascular space to the extravascular tissue to "drain" back into the intravascular space before the next inflation (208), for example to avoid accumulation of fluid in extravascular tissue. This pause is represented in FIGS. 5A-5C by the gap 508 between intervals 506. Fluid may accumulate in extravascular tissue, for example, if a protocol was employed in which the cuff is continuously inflated until the pressure in the cuff overcomes a systolic pressure. Conducting plethysmograph measurements while fluid is accumulated in extravascular tissue could adversely affect the plethysmograph output accuracy, which ideally should provide only output values that relate to intravascular fluid volume.

In an embodiment, the system 100, 400 uses (214) sensor information from a plurality of sensors and/or sensor modalities in order to enhance the accuracy of the systolic blood pressure determination (208) and/or to enhance the accuracy of the detection of another vital sign. For an intra-modality example, data received from one type of sensor (e.g. plethysmograph 102a/102b) is optionally corrected and/or normalized based on data received from a different type of sensor (e.g. an accelerometer, where movement sensed by the accelerometer near a specific plethysmograph is used to "correct" data sensed by the plethysmograph where the data is more noisy (e.g., slightly skewed as a result of the movement)) for example by improving signal to noise ratio of the plethysmograph reading, by reducing the noise component. In a helicopter transport/emergency evacuation type scenario, the at least one additional sensor 102b is used to filter out sensor noise created by the helicopter rotor blades and/or mechanical vibrations from the first sensor 102a. As another example, as an alternative to correction as described above, plethysmograph data from the vicinity of an accelerometer that shows a lot of movement is optionally discarded and/or ignored as a result of a certain level of movement detection by the accelerometer and data is instead used from a different sensor.

For an inter-modality and synergistic example, calculating the pulse using an oscillometric method allows for anticipation of the peak amplitude in the plethysmograph signal and comparison of the pulse derived from it. This for example enables better signal to noise ratio for calculating oxygen saturation from the 2 plethysmograph 102a/102b wavelengths.

In some embodiments, the system 100, 400 is programmed to choose which modality will provide the best result based on the corrective and/or normalizing methods described above. In some embodiments, the system 100, 400 is programmed to select, based for example on at least one quality criterion, the most suitable sensor for collecting data pertaining to a vital sign of interest. At one instance it may for example be determined that the oscillometric modality is comparably more suitable to measure a component of blood pressure and/or heart rate than a plethysmograph modality or vice versa. In the former, the plethysmograph modality may yet still used to determine breathing rate and/or blood saturation level.

It is noted that the expression "selection of a sensor", "choosing a sensor", "using data", and "selecting data" as well as grammatical variations thereof may be used interchangeably.

In an embodiment, once the systolic blood pressure has been determined (208), and/or subsequently diastolic blood pressure and/or any other vital signs have been measured, the patient's condition diagnosis can be rendered leading to possible treatment, which may include preventive treatment to avoid eventually diagnosed forecasted deterioration in the patient's health condition. In some embodiments, historical data descriptive of the patient's blood pressure may be analyzed and compared to give trends in the measured vital signs.

In an embodiment, the system 100, 400 is designed to give weights to different vital sign parameters. The system 100, 400 is further operative to determine, based on the weighting of the different monitored parameters and integration of the data, if a patient's condition is expected to worsen in the mid- and long term (hours or days, as opposed to identification of immediate deterioration), and/or according to the number of failing systems and/or data indicative of severity.

EXAMPLES

Reference is now made to the following examples, which together with the above descriptions illustrate some embodiments in a non-limiting fashion.

Example 1

In order to verify the accuracy of two modalities for determining heart rate, an oscillometric method as well as a plethysmograph method are used to provide data about a patient's heart rate. The level of synchronization between the oscillometric determined heart rate is compared with the timing of the peak values provided by the plethysmograph to indicate whether the heart rate readings received from the two sensors/modalities are similar, in which case the results are verified.

Example 2

Data obtained from the plethysmograph is optionally used to calculate a patient's breathing rate in the system 100, 400. The weights may be set to a constant value or, alternatively, adjusted, e.g., dynamically while the patient is being monitored. In embodiments, the value of one or more of the weights may set to be constant and the value of one or more other weights may be dynamically adjusted. The values of weights may be set or adjusted, e.g., based on data descriptive of vital signs received from the sensors, e.g., during the monitoring of the patient.

If the system 100, 400 determines that the plethysmograph values alone are not accurate enough for example, if one or more quality criteria (e.g. signal to noise ratio of plethysmograph readings) are not met, the system 100, 400 provides output to the patient through the user interface which may include an audio prompt, requesting the patient to put one hand on the chest or abdomen such that movement of the chest or abdomen can be measured using accelerometers worn by the patient on that hand. In some embodiments, both of the patient's hands are used to determine not only breathing rate but also identify breathing pattern by placing one hand on the chest and/or one hand on the abdomen (e.g. respiration patterns of adults children and/or neonates).

Example 3

In a scenario where the systolic blood pressure is 60 (i.e. very low) but the patient nevertheless exhibits a normal pulse and breathing rate, without showing trend of compensating for the (abnormally) low systolic blood pressure, the system can recheck the patient's systolic blood pressure value and alarm an attending medical professional if the re-measured value continues to reflect an abnormal number. According to the inventors, known systems do not integrate such data, lack the capability of providing corresponding output to medical personnel, and do not employ wearable devices for collecting such data.

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention, however, to the extent that any citation or reference in this application does not contradict what is stated herein, it is incorporated by reference. To the extent that section headings are used, they should not be construed as necessarily limiting.

What is claimed is:

1. A system for vital sign measuring of a patient, comprising:
    a first sensor removably attachable with a first body portion of the patient and configured to measure, when in operable position, a vital sign of the patient, wherein the first sensor comprises a first plethysmograph removably attachable to a first finger of the patient;
    at least one additional sensor removably attachable with a second body portion of the patient and configured to measure, when in operable position, a vital sign of the patient, said at least one additional sensor comprising a second plethysmograph removably attachable to a second finger of the patient;
    a pressure cuff removably attachable to the first finger between the first plethysmograph and a respective ipsilateral palm of the patient;
    an inflation device and a deflation device configured to inflate and deflate the pressure cuff, respectively; and
    a processor configured to:
        (a) command the inflation and deflation devices to inflate and deflate the pressure cuff in intervals for a plurality of times, to determine diastolic and/or systolic blood pressure, wherein:
the inflating in each of the plurality of times is at least to a slightly higher pressure than the inflating before it;
additional inflating is only performed after the initial deflating is complete;
(b) determine the diastolic blood pressure to be a pressure to which the pressure cuff was inflated when a transition in the plethysmograph reading exceeds a predefined amount;
(c) determine a level of correspondence between a first signal from the first plethysmograph and a second signal from the second plethysmograph; and
(d) determine the systolic blood pressure of the patient based on a change in said level of correspondence, when a correlation drops precipitously to a level below a certain correlation threshold.

2. The system according to claim 1, wherein the at least one additional sensor additionally comprises at least one of an accelerometer, a thermometer, a sound meter, and a digital pressure sensor.

3. The system according to claim 1, wherein the processor is located remotely from the patient.

4. The system according to claim 1, wherein signals in the system are communicated wirelessly.

5. The system according to claim 1, wherein the system is configured to be wearable by the patient.

6. The system according to claim 1, wherein at least a portion of the system is configured to be wearable by an attending medical professional.

7. The system according to claim 1, wherein the processor is further configured to determine, from received signals, at least one of: mean arterial pressure, pulse rate, breathing rate, breathing pattern, hemoglobin oxygen saturation level, motor function, temperature, and cognitive ability of the patient.

8. The system according to claim 1, wherein the level of correspondence is expressed as a correlation.

9. The system according to claim 1, where the inflation device comprises at least one of a pump and a valve.

10. A method for vital sign measuring, comprising:
removably attaching a first sensor to be in an operable position to a first body portion of the patient for measuring a vital sign of the patient, wherein the first sensor comprises a first plethysmograph removably attachable to a first finger of the patient;
removably attaching at least one additional sensor to be in an operable position to a second body portion of the patient for measuring a vital sign of the patient, wherein the at least one additional sensor comprises a second plethysmograph removably attachable to a second finger of the patient;
inflating a pressure cuff attached to the first finger between the first plethysmograph and a respective ipsilateral palm of the patient;
repeating inflating and deflating the pressure cuff in intervals for a plurality of times to determine diastolic and/or systolic blood pressure, wherein:
the inflating in each of the plurality of times is at least to a slightly higher pressure than the inflating before it;
additional inflating is only performed after the initial deflating is complete;
determining the diastolic blood pressure to be a pressure to which the pressure cuff was inflated when a transition in the plethysmograph reading exceeds a predefined amount;
determining a level of correspondence between a first signal from the first plethysmograph sensor and a second signal from the second plethysmograph sensor; and
determining the systolic blood pressure of the patient based on a change in said level of correspondence when a correlation drops precipitously to a level below a certain correlation threshold.

11. The method according to claim 10, wherein the at least one additional sensor additionally comprises an accelerometer for detecting motion of the at least a portion of the patient.

12. The method according to claim 10, wherein the determining of the level of correspondence is also between the first and second signals and a signal of a thermometer that assesses vasodilation in response to warming of the first finger of the patient.

13. The method according to claim 10, wherein the determining of the level of correspondence is also between the first and second signals and a signal of that measures a sound level of the patient.

14. The method according to claim 10, further comprising using an oscillometric method for determining the systolic blood pressure, the diastolic blood pressure, or both.

* * * * *